United States Patent [19]

Old et al.

[11] Patent Number: 4,650,756

[45] Date of Patent: Mar. 17, 1987

[54] MONOCLONAL ANTIBODIES TO CELL SURFACE ANTIGENS OF HUMAN RENAL CANCER

[75] Inventors: Lloyd J. Old, New York; Kenneth O. Lloyd, Bronx, both of N.Y.; Herbert F. Oettgen, New Canaan, Conn.; Willet F. Whitmore, New York, N.Y.; Jerzy Szkudlarek, Wroclaw, Poland; Connie L. Finstad; Donna Morrissey, both of New York, N.Y.; Shun-ichiro Ogata; Ryuzo Ueda, both of Nagoya, Japan

[73] Assignee: Sloan Kettering Institute for Cancer Research, N.Y.

[21] Appl. No.: 297,814

[22] Filed: Aug. 31, 1981

[51] Int. Cl.$^4$ .................... C12P 21/00; C12N 5/00; C12N 15/00; C12R 1/91
[52] U.S. Cl. ..................... 435/68; 435/240; 435/948; 435/172.2; 436/548
[58] Field of Search ............... 435/68, 172, 240, 241, 435/948; 424/85

[56] References Cited

U.S. PATENT DOCUMENTS 4,172,124 10/1979 Koprowski et al. ............... 435/240

OTHER PUBLICATIONS

Parham et al., "Use of a Monoclonal Antibody (W6/32) in Structural Studies of HLA-A,B,C Antigens" Journal of Immunology, vol. 123(1), (1979) pp. 342–349.
Voak, et al., "Monoclonal Anti-A from a Hybrid-Myeloma: Evaluation as a Blood Grouping Reagent", Vox Sanguinis, vol. 39, (1980) pp. 134–140.
Sacks et al., "Monoclonal Anti-B as a New Blood-Typing Reagent", Vox Sanguinis, vol. 40 (2–1981), pp. 99–104.
Ueda et al., "Cell Surface Antigens of Human Renal Cancer Defined by Autologous Typing", Journal of Experimental Medicine, vol. 150, (1979), pp. 564–579.
Dippold et al., "Cell Surface Antigens of Human Malignant Melanoma: Definition of Six Antigenic Systems with Mouse Monoclonal", Proceedings of the National Academy of Sciences, 77(10), (1980), pp. 6114–6118.
Houghton et al., "Serological Survey of Normal Humans for the Natural Antibody to Cell Surface Antigens of Melanoma", Proceedings of the National Academy of Sciences, 77(7), (1980), pp. 4260–4264.
Dippold et al., "p53 Transformation-Related Protein: Detection by Monoclonal Antibody in Mouse and Human Cells", Proceedings of the National Academy of Sciences, 78(3), (3–1981), pp. 1695–1699.
Catalogue of Cell Lines and Hybridomas—1985 ATCC, p. XV.

Primary Examiner—Thomas G. Wiseman
Assistant Examiner—J. E. Tarcza
Attorney, Agent, or Firm—Felfe & Lynch

[57] ABSTRACT

The preparation and use of monoclonal antibodies to human renal tumor cells is described. The monoclonal antibodies bind to glycoproteins of 160Kd, 120Kd and 115Kd, a glycolipid, a HLA heavy chain, group A blood and group B blood antigens.

10 Claims, No Drawings

MONOCLONAL ANTIBODIES TO CELL SURFACE ANTIGENS OF HUMAN RENAL CANCER

The invention described herein was made in the course of work under a grant or award from the Department of Health, Education and Welfare.

BACKGROUND

The present invention relates to the generation of monoclonal antibodies and their use in identifying or characterizing human renal cancer antigens. This is a useful diagnostic tool in the detection of renal cancer as well as the study of the nature of renal cancer. Immunofluorescent or enzymatic tagging agents can be bound to the highly specific antibodies using normal procedures, as required for indexing methods. Cytotoxic agents can also be bound to the highly specific antibodies to produce so called "magic bullet" type therapeutic agents which selectively destroy the cells with which the specific antibody binds.

We recently described our initial analysis of cell surface antigens of human malignant melanoma identified by mouse monoclonal antibodies (Abs)(Dippold et al. Proc. Natl. Acad. Sci. USA 77, 6114–6118 (1980)). This invention relates to a comparable analysis of human renal cancer.

BRIEF DESCRIPTION

Seventeen monoclonal antibodies derived from fusions with spleen cells of mice immunized with established culture lines of renal cancers identified nine cell surface antigenic systems. Six of the systems (gp160, $S_{25}$, gp120r, gp120 nr, gp115, and $V_1$) represent antigens not previously described. The other three systems are related to HLA-A, -B, and -C heavy chain and A and B blood group antigens. The most restricted of the newly described antigens are gp160, $S_{25}$, and gp120r. These determinants are found only on cells of renal origin, both normal and malignant, and represent differentiation antigens of human kidney. In addition to the difference in the molecular weight of two of these antigens, gp160, $S_{25}$, and gp120r can be distinguished on the basis of differential expression on a panel of cultured renal cancers and normal kidney epithelium and fetal kidney cells. Glycoproteins bearing gp120r share a determinant with renal gp120nr (as indicated by sequential precipitations with monoclonal antibodies that detect gp120r and gp120nr), but gp120nr is found on a broader range of cell types, including fibroblasts and cell lines derived from ovarian, bladder, and colon cancers. The two other new systems, gp115 and $V_1$, have characteristics of broadly occurring differentiation antigens but can be distinguished from each other and from gp120nr by differences in molecular weight, heat stability ($V_1$ is a heat-stable determinant), and differential expression on cell types of diverse origin.

These systems can be used to characterize and study the nature of renal cancer. Thus, comparison of the $S_{25}$ and the gp160 phenotypes of different renal cancer cell lines and cultures of normal kidney clearly distinguish these two systems.

DESCRIPTION

This study of renal cancer and our recent study of melanoma (Dippold, et al. Proc. Natl. Acad. Sci. USA 77, 6614–6118 (1980)), have generated a series of mouse Abs that define 12 new systems of human cell surface antigens. Six of these have been identified as glycoproteins (gp95, gp150, gp160, gp120r, gp120nr, and gp115), three are heat-labile antigens that could not be immunoprecipitated from labeled cell extracts ($S_{25}$, $M_{19}$, and $R_8$), and three are heat-stable antigens, presumably glycolipids ($O_5$, $R_{24}$, and $V_1$). The use of a standard panel of cultured human cells allows ready comparisons of the reactivity of these monoclonal antibodies in direct serological tests and absorption analysis, and each of the antigenic systems has a distinct pattern of distribution on the cell panel, in terms of both qualitative and quantitative expression of antigens. On the basis of their distribution on different cell types, these 12 antigenic systems can be further classified into three groups: (i) those with characteristics of restricted differentiation antigens (e.g., the renal-specific gp160, $S_{25}$, and gp120r antigens and the $R_{24}$ antigen of melanoma and melanocytes), (ii) more broadly represented differentiation antigens (e.g., gp95, gp150, $M_{19}$, gp120nr, and $V_1$), and (iii) antigens expressed by every human cell type tested (e.g., $O_5$ species antigen).

It has also been found that the cell lines derived from stage I renal cancer (confined to the kidney) are gp160+, whereas cell lines from metastatic renal cancers are gp160−. Whether this indicates that cancer cells developing metastatic potential lose gp160 expression, or that gp160+ and gp160− renal cancers are derived from separate cell lineages is not determined; however, identifying the cell types in normal kidney that express gp160 and other antigens found on renal cancer should give information about the cellular origins of renal cancer.

These serological probes provided by the invention can identify kidney-specific antigens and are of particular interest in the study of kidney structure and function. In addition, some of the more broadly reacting antibodies are useful in studying other tumors—e.g., $V_1$ which distinguishes astrocytomas from melanomas.

The importance of parallel biochemical and serological characterizations of antigens identified by Abs is illustrated by the analysis of gp120r and gp120nr. Five Abs in this series immunoprecipitated a 120,000-dalton component from labeled extracts of SK-RC-7 renal cancer cells. Preclearing the extract with one of these Abs (Ab $S_6$) removed the 120,000-dalton component identified by Ab $S_{23}$, indicating that the two Abs were reacting with the same molecule. However, the antigenic determinant detected by Ab $S_6$ and Ab $S_{23}$ can be distinguished in M-MHA tests and absorption analysis. Ab $S_{23}$ detected a kidney-specific antigen, whereas Ab $S_6$ reacted with a much broader range of cell types. These results can be explained by postulating two species of gp120 molecules, both carrying the epitope identified by Ab $S_6$ but only one with the epitope identified by Ab $S_{23}$. In agreement with this interpretation, supernatants after clearing with Ab $S_{23}$ still reacted with Ab $S_6$, even though no antigen precipitating with Ab $S_{23}$ remained. The epitope identified by Ab $S_{23}$ is found only on cells of renal origin and, because of this restricted distribution, it is referred to as gp120r. The more widely distributed epitope has been designated "nr" to indicate its nonrestricted nature. gp120r and gp120nr may be the products of two separate genes or of a single gene whose product is modified in renal cells. Similar, although less striking, discrepancies in the cellular distribution of antigens identified by different monoclonal antibodies immunoprecipitating gp95 or gp150 molecules have also been explained on the basis of different epitopes being recognized (Dippold, et al. Proc. Natl. Sci. USA 77, 6114–6118(1980)).

EXPERIMENTAL

Tissue Culture. The renal cancer cell lines (Ueda et al. J. Exp. Med. 150, 564–589 (1979)) and tumor cell lines (Carey, et al. Proc. Natl. Acad. Sci. USA 73, 3278–3282 (1976)) have been described. Methods for the short-term culture of normal kidney epithelium have also been described (Ueda (supra)). Cultures were maintained in Eagle's minimal essential medium supplemented with 2 mM glutamine, 1% nonessential amino acids, 100 units of penicillin per ml, 1 μg of streptomycin per ml, and 10% (vol/vol) fetal bovine serum. Cultures were regularly tested for mycoplasma, fungi, and bacteria, and contaminated cultures were discarded.

Serological Procedures. The mouse mixed hemadsorption assay (M-MHA) was performed by the method of Fagraeus et al. Immunology 9, 161–175 (1965), as modified to detect mouse antibody. Serological procedures for direct test and absorption analysis are described in Dippold et al (supra); Ueda et al (supra) and Carey et al (supra).

Immunizations. (BALB/c×C57BL/6)F$_1$ female mice were immunized with established renal cancer cell lines (See Table 1). For the initial immunization, 1×10$^7$ renal cancer cells were injected subcutaneously without adjuvant. Subsequent immunizations were carried out at intervals of 3-4 weeks by intraperitoneal inoculation of 1×10$^7$ renal cancer cells. Immunized mice were sacrificed 3 days after the last immunization.

Derivation of Mouse Abs. The fusion of immune spleen cells with mouse myeloma MOPC-21 NS/1 cells was performed as described (Dippold et al (supra) and Kohler and Milstein, Nature (London) 236, 495–497 (1975)). Fused cells (5–8×10$^5$) in 1 ml of selective medium containing hypoxanthine, aminopterin, and thymidine were added to wells of tissue culture plates (Costar no. 3524, 24 wells per plate). Hybridoma cultures were subcloned at least three times by limiting dilution on a feeder layer of 1–3×10$^5$ mouse peritoneal macrophages. Culture supernatants were monitored for antibody activity on a panel of cultured cells consisting of two renal cancer cell lines (including the immunizing line), AJ astrocytoma, SK-MEL-33 and -37 melanomas, ME-180 cervix cancer, WI-38 fetal cells, VERO adult and fetal kidney epithelium, and fetal brain cells. Antibody subclass was determined by double diffusion in agar with anti-Ig heavy chain specific reagents (Bionetics, Kensington, M. D.). Cultures of cloned hybridomas were injected subcutaneously into nu/nu mice (Swiss background) and were also stored in liquid nitrogen and maintained on deposit at Sloan-Kettering Institute for Cancer Research, 1275 York Avenue, New York, N.Y. 10022, under designations corresponding to the monoclonal antibodies produced by each hybridoma as follows: M$_1$, S$_4$, S$_6$, S$_7$, S$_{22}$, S$_{23}$, S$_{24}$, S$_{25}$, S$_{26}$, S$_{27}$, and V$_1$. These hybridoma cell lines have been made publicly available by deposit with the American Type Culture Collection, 1230 Parklawn Drive, Rockville, Md. 20852, and bear the following designations:

| | |
|---|---|
| M1 | HB |
| S4 | HB 8541 |
| S6 | HB 9034 |
| S7 | HB 9035 |
| S22 | HB 8542 |
| S23 | HB 8540 |
| S24 | HB 9037 |
| S25 | HB 9069 |
| S26 | HB 9044 |
| S27 | HB 8428 |
| V1 | HB 8429 |

Sera from mice with progressively growing tumors were collected, stored at −70° C., and used for serological and biochemical characterization.

Immunoprecipitation Procedures. Cells were metabolically labeled with [$^3$H] glucosamine in complete Eagle's medium containing 15 uCi of [$^3$H] glucosamine (New England Nuclear; 30–60Ci/mmol; 1 Ci=3.7×10$^{10}$ becquerels) per ml for 48 hr at 37° C.; the labeled cells were extracted with 0.5% Nonidet P-40 (NP-40) in Tris buffer as described (Ogata et al. Proc. Natl. Acad. Sci. USA 78, 770–774 (1981)) except that the 3M KCl treatment was ommitted. Immunoprecipitation was carried out by mixing a portion of the cell extract (1×10$^5$ cpm) with 2 μl of mouse serum and 20 μl of rabbit anti-mouse Ig serum (Cappel Laboratories, Cochranville, PA) in Tris buffer. Immune complexes were isolated by using Staphylococcus aureus and analyzed by NaDodSO$_4$/polyacrylamide gel electrophoresis as described (Dippold et al (supra)). [$^{35}$S] Methionine-labeled samples were immunoprecipitated in a similar manner, except that Sepharose-rabbit F (ab')$_2$ anti-mouse Ig was used for isolating the complexes. To determine the pI of the antigens, immunoprecipitates were examined by two-dimensional electrophoresis by the O'Farrell procedure (O'Farrell, P. H. Biol. Chem. 250, 4007–4021 (1975)) modified as described (Ogata, et al (supra)). From the five fusions of NS-1 myeloma with three different renal cancer cell lines, 17 antibody-producing clones were selected for detailed analysis (Table 1). The serological specificity of these antibodies was tested on a panel of 47 established cell lines [13 renal cancers, 5 melanomas, gliomas neuroblastomas, 15 epithelial cancers, 5 B-cell lines K562 (an erythroid leukemia), 2 T-cell lines (MOLT-4 and T-45), and monkey kidney cells (VERO)]. In addition, the antibodies were tested against short-term cultures of normal kidney epithelium, fibroblasts, and fetal tissues (brain, fibroblasts, and kidney). Human, sheep, rat and bovine erythrocytes were also examined. In most cases, serological analysis consisted of both direct and absorption tests.

These serological studies in conjunction with immunochemical analysis defined nine distinct antigenic systems. Three systems (gp160, S$_{25}$, and gp120r) were restricted to normal and malignant renal cells, three systems (gp120nr, gp115, and V$_1$) were more widely distributed, and three systems were identified as HLA-A, -B, -C heavy chain and A and B blood group antigens.

gp 160 Antigenic System. Five Abs in this series (S$_4$, S$_7$, S$_{11}$, S$_{24}$, and M$_1$) identifies a 160,000-dalton glycoprotein that showed a high degree of specificity for human kidney cells. gp 160 is a rather basic component with pI 7.5. By M-MHA tests, gp160 could be demonstrated on all cultures of normal kidney epithelium, 2 of 3 cultures of fetal kidney, and 7 of 13 established lines of renal cancer (Table 2). These results were confirmed in absorption tests. No other cell type, normal or malignant, was found to express the gp160 antigen, including VERO, a cell line derived from monkey kidney.

$S_{25}$ Antigenic System. The antigen detected by Ab $S_{25}$ also is restricted to human cells of renal origin (Table 2). The $S_{25}$ determinant is heat labile, suggesting that it resides on a protein or glycoprotein, but Ab $S_{25}$ did not precipitate any detectable component from [$^{35}$S] methionine-labeled or [$^3$H] glucosamine-labeled SK-RC-7 cells. Comparison of the $S_{25}$ and the gp160 phenotypes of different renal cancer lines and cultures of normal kidney clearly distinguished these two systems. For example, SK-RC-6 and A-498 are gp160$^+$/$S_{25}^-$ and SK-RC-8 is gp160$^-$/$S_{25}^+$. In addition, all nine cultures of normal kidney epithelium were gp160$^+$, whereas five of these cultures lacked $S_{25}$ expression.

gp120r and gp120nr Antigenic Systems. Five Abs ($S_{23}$, $S_{26}$, $S_{27}$, $S_6$, and $S_1$) immunoprecipitated a 120,000-dalton glycoprotein from [$^{35}$S] methionine- or [$^3$H] glucosamine-labeled lysates of SK-RC-7 cells. Analysis under reducing and nonreducing conditions gave the same results. The pIs of gp120 identified by prototype Ab $S_6$ and Ab $S_{23}$ were identical (4.9–5.2). A further indication of the relatedness of the gp120 components identified by these two groups of Abs came from sequential immunoprecipitation tests. Pretreatment of [$^3$H] glucosamine-labeled lysates of SK-RC-7 with Ab $S_6$ removed all antigen reactive with Ab $S_{23}$. In contrast, M-MHA tests and absorption analysis (Table 2) showed that these gp120 antibodies identified two serologically distinct gp120 epitopes that distinguish two classes of gp120 molecules: gp120r (restricted) and gp120nr (nonrestricted).

gp120r, identified by Ab $S_{23}$, had a highly restricted distribution, expression being limited to normal kidney epithelium and certain renal cancers. The other gp120 epitope, gp120nr, identified by Ab $S_6$, was found on a wide range of cultured cells including fetal and adult fibroblasts and cell lines derived from ovarian, bladder, and colon cancers. gp120r and gp120nr determinants differ in their expression on renal cancer cell lines: all cell lines carry the gp120nr epitope, whereas SK-RC-2, -21, -29, and Caki-1 lack gp120r determinants. The specificity of Ab $S_{23}$ for cells of renal origin resembles the reactivity of Ab $S_{25}$ and, most particularly, antibodies identifying the gp160 system. However, in addition to the molecular weight differences in the gp160 and gp120 antigens, these three kidney-specific antigenic systems can be distinguished on the basis of absorption analysis with selected normal or malignant kidney cells—e.g., SK-RC-6 and A-498 are gp160$^+$/$S_{25}^-$/gp120r$^+$; fetal kidney is gp160$^+$ or $-$/$S_{25}^+$/gp120r$^-$.

gp115 Antigenic system. Ab $S_{22}$ immunoprecipitated a 115,000-dalton glycoprotein from [$^3$H] glucosamine- or [$^{35}$S] methionine-labeled lysates of SK-RC-7 cells under both reduced and nonreduced conditions (FIG. 1). In direct M-MHA tests, high reactivity (titers, 1–10,000×10$^{-3}$) was restricted to certain renal cancer cells and normal kidney epithelium (Table 2). Absorption analysis, however, revealed that the gp 115 antigen was expressed by various cell types.

$V_1$ Antigenic System. Ab $V_1$ did not immunoprecipitate any labeled component from [$^3$H] glucosamine- or [$^{35}$S] methionine-labeled lysates of SK-RC-7 cells. Absorption tests indicated that the antigen is heat stable (5 mins. at 100° C.), suggesting that it is a glycolipid. Two features of the $V_1$ (Table 2) system are of particular interest: (a) it identifies a subset of bladder and breast cancers do not express $V_1$, and (b) $V_1$ is not found on astrocytomas, whereas melanomas are strong $V_1$ expressors. This clear distinction between astrocytoma and melanoma, whose embryonic derivations are closely related, has not been seen with other Abs.

HLA Heavy Chain. Ab $S_{21}$ immunoprecipitated a 45,000- and a 12,000-dalton component from [$^{35}$S] methionine-labeled SK-RC-7 lysates. The determinant detected by Ab $S_{21}$ in direct and absorption tests was present on virtually every human cell type with the exception of human erythrocytes (Table 2). Of all the human cultured cells tested, the only cell lines not reactive with Ab $S_{21}$ in direct MHA tests were ME-180 and SK-MEL-19; the SK-MEL-19 melanoma cell line is known from previous work to express little or no HLA-A, -B, -C antigens. The molecular weights of the components precipitated by Ab $S_{21}$ and the results of the serological survey of human cells indicated that Ab $S_{21}$ detected HLA but did not distinguish between a determinant on the heavy chain or on the $\beta_2$m chain. The fact that isolated human $\beta_2$m did not inhibit the reactivity of Ab $S_{21}$ suggests specificity for HLA heavy chain.

A and B Blood Group Antigens. Two of the three renal cancer lines used for immunization (Table 1) express blood group A or B antigens on their cell surfaces; SK-RC-7 is B$^+$ and SK-RC-28 is A$^+$. SK-RC-6 is derived from a type O individual and is negative for A and B reactivities. To detect Abs reacting with blood group antigens, hybridoma supernatants were screened for hemagglutinating antibody by using A, B, AB, or O erythrocytes. B (but not A) agglutinating activity was found in 4 of 462 supernatants from the anti-SK-RC-7 (fusion, and A (but not B) agglutinating activity was found in 3 or 225 supernatants from the anti-SK-RC-28 fusion. No agglutination of type O erythrocytes was found in supernatants from anti-SK-RC-7, -28 or -6 fusions. Two monoclonal antibodies with hemagglutinin activity were derived from these fusions. The hemagglutination titer of Ab $M_2$ (nu/nu serum) for A and AB erythrocytes was 10$^{-4}$; B erythrocytes were not agglutinated by Ab $M_2$. The hemagglutination titer of Ab $S_8$ (nu/nu serum) for B and AB erythrocytes was 4×10$^{-5}$; A type erythrocytes were not agglutinated by Ab $S_8$. Table 3 summarizes inhibition tests with Ab $S_8$ and Ab $M_2$ using glycoprotein and mucin extracts having A, B, H, and Lewis$^a$ blood group reactivity. The results confirmed the A specificity of Ab $M_2$ and the B specificity of Ab $S_8$.

TABLE 1

Derivation of mouse hybridomas producing Abs reacting with surface antigens of human renal cancer cells

| Exp. | Renal cancer cell line used for immunizations | Immunizations, no. | Results of initial fusion and antibody screening | | Clones isolated and analyzed, no. | Abs characterized |
|---|---|---|---|---|---|---|
| | | | Growth/wells, no./no. | Positive wells, no. | | |
| 1 | SK-RC-7 | 8 | 462/480 | 450 | 6 | $S_1(\gamma 1), S_4(\gamma 2a)^*, S_6(\gamma 1)^*, S_7(\gamma 2a), S_8(\mu)^*, S_{11}(\gamma 2a)$ |
| 2 | SK-RC-7 | 2 | 175/336 | 50 | 7 | $S_{21}(\gamma 1)^*, S_{22}(\gamma 1)^*, S_{23}(\gamma 1)^* S_{24}(\gamma 1), S_{25}(\gamma 1)^*, S_{26}(\gamma 1), S_{27}(\gamma 1)$ |
| 3 | SK-RC-7 | 1 | 43/320 | 0 | 0 | None |

TABLE 1-continued
Derivation of mouse hybridomas producing Abs reacting with surface antigens of human renal cancer cells

| Exp. | Renal cancer cell line used for immunizations | Immunizations, no. | Results of initial fusion and antibody screening Growth/wells, no./no. | Positive wells, no. | Clones isolated and analyzed, no. | Abs characterized |
|---|---|---|---|---|---|---|
| 4 | SK-RC-6 | 8 | 64/72 | 64 | 2 | $V_1(\gamma 1)^*, V_2(\gamma 1)$ |
| 5 | SK-RC-28 | 3 | 225/476 | 212 | 2 | $M_1(\gamma 1), M_2(\mu)^*$ |

*Prototype Abs (see Tables 2 and 3).

TABLE 2

| Cells | AbS$_4$ Titer ×10$^{-3}$ | Abs. | AbS$_{25}$ Titer ×10$^{-3}$ | Abs. | Ab S$_{23}$ Titer ×10$^{-3}$ | Abs. | Ab S$_6$ Titer ×10$^{-3}$ | Abs. | Ab S$_{22}$ Titer ×10$^{-3}$ | Abs. | Ab V$_1$ Titer ×10$^{-3}$ | Abs. | Ab S$_{21}$ Titer ×10$^{-3}$ | Abs. |
|---|---|---|---|---|---|---|---|---|---|---|---|---|---|---|
| Epithelial cancers: | | | | | | | | | | | | | | |
| Renal | | | | | | | | | | | | | | |
| SK-RC-1(AA) | 50 | + | — | + | 1 | + | 50 | + | — | + | 500 | + | 50000 | + |
| SK-RC-2(AB) | — | — | — | — | — | — | 50 | + | — | + | 500 | + | 5000 | + |
| SK-RC-4(AE) | 50 | + | 500 | + | 50 | + | 50 | + | 5000 | + | 10000 | + | 5000 | + |
| SK-RC-6(AG) | 50 | + | — | — | 10 | | 1000 | + | 5 | + | 10000 | + | 100000 | + |
| SK-RC-7(AX) | 50 | + | 500 | + | 1 | + | 500 | + | 10000 | + | 10000 | + | 50000 | + |
| SK-RC-8(BE) | — | — | 1 | + | 1 | + | 50 | + | 50 | + | 50 | + | 500 | + |
| SK-RC-9(BM) | — | — | — | + | — | + | 500 | + | 50 | + | 5000 | + | 50000 | + |
| SK-RC-11(BZ) | 5 | + | — | + | 1 | + | 1000 | + | — | + | 10000 | + | 50000 | + |
| SK-RC-21(EB) | — | — | — | — | — | — | 500 | + | — | + | 1 | + | 50000 | + |
| SK-RC-28(EU) | 50 | + | — | + | 500 | + | 5000 | + | — | + | 500 | + | 100000 | + |
| SK-RC-29(BW) | — | — | — | — | — | — | 50 | + | — | + | 5000 | + | 50000 | + |
| A-498 | 10 | + | — | — | — | + | 50 | + | — | + | 10000 | + | 100 | + |
| CaKi-1 | — | — | — | — | — | — | 50 | + | — | + | 10000 | + | 100 | + |
| Bladder | | | | | | | | | | | | | | |
| RT-4 | — | — | — | — | — | — | — | — | — | + | 5000 | + | 50 | + |
| 5637 | — | — | — | — | — | — | — | — | — | + | — | — | 10 | + |
| T-24 | — | — | — | — | — | — | 5 | + | — | + | — | — | 10000 | + |
| 253J | — | — | — | — | — | — | 5 | + | — | + | 5000 | + | 5000 | + |
| Breast | | | | | | | | | | | | | | |
| AlAb | — | — | — | — | — | — | — | — | — | — | 5 | + | 500 | + |
| BT-20 | — | — | — | — | — | — | — | — | — | — | — | — | 50 | + |
| MCF-7 | — | — | — | — | — | — | — | — | — | — | 10000 | + | 1000 | + |
| SK-BR-3 | — | — | — | — | — | — | — | — | — | — | 10000 | + | 10 | + |
| Cervix | | | | | | | | | | | | | | |
| ME-180 | — | — | — | — | — | — | — | — | — | — | — | + | — | + |
| Colon | | | | | | | | | | | | | | |
| HT-29 | — | — | — | — | — | — | 5 | + | — | — | — | + | 50 | + |
| SW-1222 | — | — | — | — | — | — | — | — | — | — | 500 | + | 5 | + |
| Lung | | | | | | | | | | | | | | |
| SK-LC-LL | — | — | — | — | — | — | — | — | — | + | 1 | + | 5 | + |
| SK-LUCl-6 | — | — | — | — | — | — | 50 | + | — | — | 10000 | + | 50000 | + |
| Ovary | | | | | | | | | | | | | | |
| SK-OV-3 | — | — | — | — | — | — | — | — | 0.5 | + | — | + | 50 | + |
| Testicular | | | | | | | | | | | | | | |
| SK-GR-1 | — | — | — | — | — | — | — | — | — | — | — | + | 1 | + |
| Astrocytomas: | | | | | | | | | | | | | | |
| AJ, AS, BE | — | — | — | — | — | — | 5 | + | — | + | — | — | 500 | + |
| Melanomas: | | | | | | | | | | | | | | |
| SK-MEL-13,28,29,37,41 | — | — | — | — | — | — | — | — | — | — | 5000 | + | 5000 | + |
| SK-MEL-19 | — | — | — | — | — | — | — | — | — | — | 5000 | + | — | + |
| Neuroblastomas: | | | | | | | | | | | | | | |
| SK-NMC, SK-NSH | — | — | — | — | — | — | — | — | — | — | 1 | + | 100 | + |
| Lymphoblastoid cells: | | | | | | | | | | | | | | |
| EBV B cells | | | | | | | | | | | | | | |
| AX, BE, EU | — | | — | | — | | — | | — | | | + | | + |
| Burkitt's lymphomas | | | | | | | | | | | | | | |
| Raji, Daudi | — | | — | | — | | — | | — | | | + | | + |
| T cells | | | | | | | | | | | | | | |
| MOLT-4, T-45 | — | | — | | — | | — | | — | | — | | | + |
| Normal Human Cells: | | | | | | | | | | | | | | |
| Kidney epithelium | | | | | | | | | | | | | | |
| ID | | | — | — | 10 | + | 5 | + | 1 | + | 5 | + | 25 | + |
| EQ, HY | 10 | + | — | — | 1.5 | + | 5 | + | 1 | + | 5 | + | 25 | + |
| GM, FR | 3 | + | 3 | + | 3 | + | 5 | + | 1 | + | 5 | + | 25 | + |
| El, IJ | 3 | + | — | + | 1.5 | + | 5 | + | 1 | + | 5 | + | 25 | + |
| EG, GR, IB | 0.5 | + | — | — | 0.5 | + | 5 | + | 1 | + | 5 | + | 25 | + |
| Fetal kidney | | | | | | | | | | | | | | |
| C-4 | 0.5 | + | 2 | + | — | — | >5 | + | >5 | + | >5 | + | >5 | + |
| C-6 | — | — | 2 | + | — | — | >5 | + | >5 | + | >5 | + | >5 | + |
| C-8 | 0.5 | + | 2 | + | — | — | >5 | + | >5 | + | >5 | + | >5 | + |

TABLE 2-continued

| Cells | AbS₄ Titer ×10⁻³ | Abs. | AbS₂₅ Titer ×10⁻³ | Abs. | Ab S₂₃ Titer ×10⁻³ | Abs. | Ab S₆ Titer ×10⁻³ | Abs. | Ab S₂₂ Titer ×10⁻³ | Abs. | Ab V₁ Titer ×10⁻³ | Abs. | Ab S₂₁ Titer ×10⁻³ | Abs. |
|---|---|---|---|---|---|---|---|---|---|---|---|---|---|---|
| Adult skin fibroblasts | — | — | — | — | — | — | 5 | + | — | — | — | — | 5 | + |
| Fetal lung fibroblasts | — | — | — | — | — | — | 1.5 | + | 0.5 | + | 0.5 | + | 10 | + |
| Fetal brain | — | — | — | — | — | — | | | | + | | — | 10 | + |
| Erythrocytes | | — | | | | | | — | | | | — | | — |
| Xenogeneic cells: | | | | | | | | | | | | | | |
| Monkey kidney | | | | | | | | | | | | | | |
| Vero | — | — | — | — | — | — | 5 | + | — | — | — | — | — | — |
| Sheep erythrocytes | | — | | | | | | — | | | | — | | — |

Under "Titer," — indicates no reaction in direct tests at a dilution of 1,200 Abs absorption tests. Sera (diluted to end point) were absorbed with the indicated cell type and tested for residual activity for SK-RC-7 (AbS₂, Ab S₂₂, Ab S₂₁), SK-RC-4(Ab S₂₅), SK-RC-6(AB V₁), or SK-RC-28 target cells (Ab S₂₃);
+, complete absorption;
—, no absorption.

TABLE 3

Ab M₂ and Ab S₈: Inhibition tests with blood group glycoproteins*

| Glycoprotein | Amount of glycoprotein required for inhibition, μg/ml | |
|---|---|---|
| | Ab M₂⁺ | Ab S₈⁺⁺ |
| Human A glycoprotein (Sullivan) | 1.3 | 120.0 |
| Human B glycoprotein (Beach) | 450.0 | 1.2 |
| Human O(H) glycoprotein (Tighe) | 246.0 | 123.0 |
| Human Le* glycoprotein (N-1) | 475.0 | 237.0 |
| Porcine A + H gastric mucin | 3.0 | 550.0 |
| Porcine A gastric mucin (67) | 4.6 | 437.0 |
| Porcine H gastric mucin (66) | 437.0 | 449.0 |

*Blood group glycoproteins were kindly provided by E.A. Kabat and have been described (9).
⁺Agglutination assay with A erythrocytes using 1:10,000 dilution of M₂.
⁺⁺Agglutination assay with B erythrocytes using 1:10,000 dilution of S₈.

What is claimed is:

1. Antibody producing hybridoma cell lines characterized by the production of nonoclonal antibodies recognizing malignant human renal cells wherein said cell lines are selected from the group consisting of ATCC HB 9079, ATCC HB 8541, ATCC HB 9034, ATCC HB 9035, ATCC HB 8542, ATCC HB 8540, ATCC HB 9037, ATCC HB 9069, ATCC HB 9044, ATCC HB 8428, and ATCC HB 8429.

2. Monoclonal antibodies recognizing malignant human renal cells and produced by hybridoma cell lines selected from the group consisting of ATCC HB 9079, ATCC HB 8541, ATCC HB 9034, ATCC HB 9035, ATCC HB 8542, ATCC HB 8540, ATCC HB 9037, ATCC HB 9069, ATCC HB 9044, ATCC HB 8428, and ATCC HB 8429.

3. Monoclonal antibodies of claim 2 recognizing the gp160 antigenic system in human renal cells.

4. Monoclonal antibodies of claim 2 recognizing the S₂₅ antigenic system in human renal cells.

5. Monoclonal antibodies of claim 2 recognizing the gp120r or gp120nr antigenic system in human renal cells.

6. Monoclonal antibodies of claim 2 recognizing the gp115 antigenic system in human renal cells.

7. Monoclonal antibodies of claim 2 recognizing the V₁ antigenic system in human renal cells.

8. Method for differentiating between normal and malignant human renal cells which comprises contacting a human renal cell specimen with a human monoclonal antibody produced by a hybridoma cell line selected from the group consisting of ATCC HB 9079, ATCC HB 8541, ATCC HB 9034, ATCC HB 9035, ATCC HB 8542, ATCC HB 8540, ATCC HB 9037, ATCC HB 9069, ATCC HB 9044, ATCC HB 8428, and ATCC HB 8429.

9. Method of claim 8 wherein said specimen is separately contacted with a plurality of said monoclonal antibodies each of which is different.

10. Monoclonal antibodies recognizing human renal cell antigenic systems selected from the group consisting of gp160, S25, gp120r, gp120nr, gp115 and V1.

* * * * *